United States Patent
Wells et al.

(10) Patent No.: US 8,192,406 B2
(45) Date of Patent: Jun. 5, 2012

(54) ANCHOR HAVING FILL PORT FOR USE WITH AN IMPLANTABLE THERAPY DELIVERY ELEMENT

(75) Inventors: Patrick D. Wells, Minneapolis, MN (US); Michael D. Baudino, Coon Rapids, MN (US)

(73) Assignee: Medtronic, Inc, Minneapolis, MN (US)

( * ) Notice: Subject to any disclaimer, the term of this patent is extended or adjusted under 35 U.S.C. 154(b) by 655 days.

(21) Appl. No.: 12/349,065

(22) Filed: Jan. 6, 2009

(65) Prior Publication Data

US 2010/0174240 A1   Jul. 8, 2010

(51) Int. Cl.
*A61M 5/32* (2006.01)
(52) U.S. Cl. .................... 604/175; 604/174; 607/132
(58) Field of Classification Search .............. 604/174, 604/175; 607/32, 132
See application file for complete search history.

(56) References Cited

U.S. PATENT DOCUMENTS

| 4,743,229 | A | * | 5/1988 | Chu ................... 604/82 |
| 5,036,862 | A | | 8/1991 | Pohndorf |
| 5,423,763 | A | * | 6/1995 | Helland et al. ............. 604/174 |
| 5,584,874 | A | | 12/1996 | Rugland et al. |
| 5,702,372 | A | | 12/1997 | Nelson |
| 6,139,570 | A | * | 10/2000 | Saadat et al. ............. 607/105 |
| 6,553,265 | B1 | | 4/2003 | Fischer, Sr. |
| 6,915,901 | B2 | | 7/2005 | Feinberg et al. |
| 6,999,819 | B2 | | 2/2006 | Swoyer et al. |
| 7,082,337 | B2 | * | 7/2006 | Sommer et al. ............. 607/132 |
| 7,184,841 | B1 | | 2/2007 | Bodner et al. |
| 7,369,894 | B2 | | 5/2008 | Gerber |
| 2005/0021119 | A1 | * | 1/2005 | Sage et al. ............. 607/122 |
| 2006/0235484 | A1 | * | 10/2006 | Jaax et al. ............. 607/46 |
| 2006/0264803 | A1 | * | 11/2006 | Lui et al. ............. 604/19 |

FOREIGN PATENT DOCUMENTS

| WO | 2009/052134 A1 | 4/2009 |
| WO | 2009052134 A1 | 4/2009 |

OTHER PUBLICATIONS

PCT International Search Report and Written Opinion dated May 18, 2010.
Partial International Search Report dated Feb. 2, 2010.

\* cited by examiner

*Primary Examiner* — Kevin C Sirmons
*Assistant Examiner* — Emily Schmidt
(74) *Attorney, Agent, or Firm* — Beth L. McMahon

(57) ABSTRACT

An anchor for securing a therapy delivery element in a desired location within a living body is disclosed. The anchor includes an anchor body having a space, which may be a main channel, to receive the therapy delivery element. A fill port is provided in the anchor body to introduce an adhesive into the space when the therapy delivery element is positioned within the space. In one embodiment, the fill port is coupled to a fill port extension that transfers the adhesive from a dispenser located a distance from the fill port into the space. Multiple fill ports, any of which may be coupled to a respective fill port extension, may be provided to introduce the adhesive at various locations of the space. One or more of the fill ports may extend into multiple side channels to introduce the adhesive at various locations of the space.

29 Claims, 12 Drawing Sheets

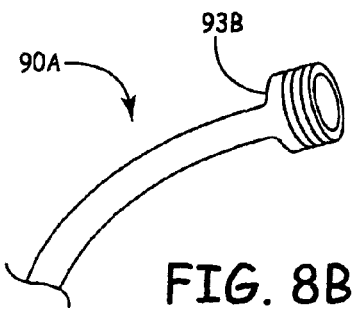
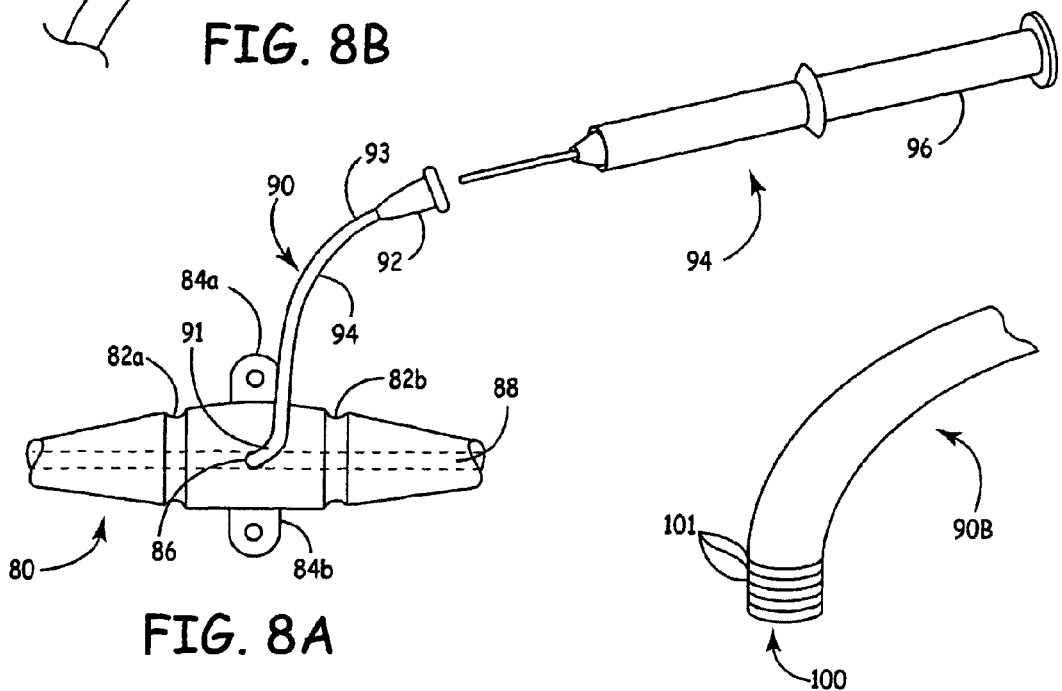
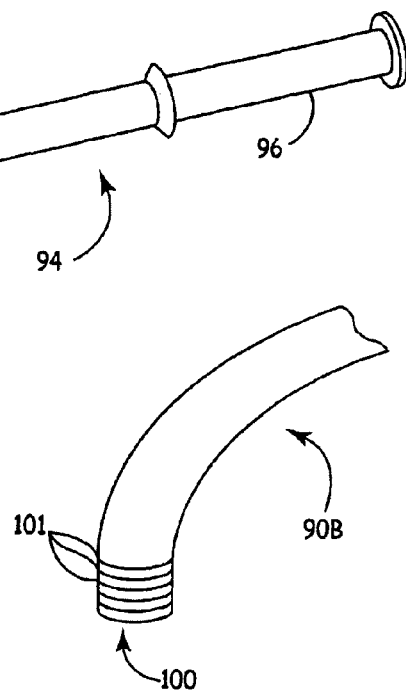
FIG. 8B
FIG. 8A
FIG. 8C
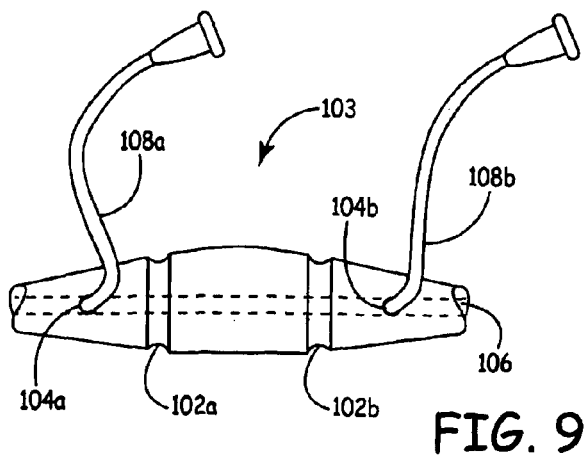
FIG. 9

ANCHOR HAVING FILL PORT FOR USE WITH AN IMPLANTABLE THERAPY DELIVERY ELEMENT

FIELD OF THE INVENTION

This disclosure relates to medical devices and more particularly to an implantable anchor for use in securing a therapy delivery element such as a stimulation lead or catheter in place within a living body.

BACKGROUND OF THE INVENTION

The medical device industry produces a wide variety of electronic and mechanical devices for treating medical conditions. Depending upon the medical condition, medical devices can be surgically implanted or connected externally to the patient receiving treatment. Clinicians use medical devices alone or in combination with therapeutic substance therapies and surgery to treat medical conditions. For some medical conditions, medical devices provide the best, and sometimes the only, therapy to restore an individual to a more healthful condition and a fuller life.

Various types of medical devices exist to treat a wide variety of conditions. For instance, electrical stimulators such as neurostimulators and microstimulators are used to treat conditions associated with chronic pain, movement disorders, incontinence, gastric disorders, depression, sexual dysfunction, and other types of conditions. As another example, devices such as pacemakers and defibrillators are used to treat heart conditions. Still other medical devices deliver substances to a living body, as may be used to treat diabetes, as one example.

Medical devices that deliver electrical stimulation may be provided with therapy delivery elements that comprise one or more stimulation leads. When a stimulation lead is inserted or implanted, it is typically anchored using a lead anchor to fix the stimulation lead to tissue. The lead anchor is provided to prevent the stimulation lead from migrating away from a specifically selected stimulation site.

Anchors may also be beneficially used to secure a therapy delivery element that comprises a catheter at a desired location. Such catheters may be used to deliver a substance to a predetermined position within a body. As was the case with stimulation leads, anchors may be needed to ensure that a catheter does not migrate such that the substance is no longer being delivered at the desired location. Anchors are also beneficial in providing support and structure to a catheter, which may have relatively thin, flexible walls.

Clinicians inserting and anchoring therapy delivery elements typically prefer to perform the procedure rapidly, in a minimally invasive manner, and fix the therapy delivery element in a manner that reduces the opportunity for the therapy delivery element to migrate if practicable. Examples of some previous anchors are shown in U.S. Pat. No. 6,134,477 "Adjustable Medical Lead Fixation System" by Knuteson (Oct. 17, 2000); U.S. Pat. No. 5,484,445 "Sacral Lead Anchoring System" by Knuth (Jan. 16, 1996); and, U.S. Pat. No. 5,843,146. "Adjustable Medical Lead Anchor" by Cross, Jr. (Dec. 1, 1998).

There is a need for an anchor that facilitates minimally invasive procedures, facilitates rapid placement to reduce procedure time, and has many other improvements.

SUMMARY OF THE INVENTION

The current disclosure describes an implantable therapy delivery system having an anchor that includes a fill port to introduce medical grade adhesive into a space of the anchor. When the therapy delivery element is positioned within this space, introduction of the medical adhesive into the space helps retain the anchor at a desired location relative to the therapy delivery element. Use of the fill port eliminates the need to apply the medical adhesive to a desired location on a surface of the therapy delivery element, slide the anchor into this desired location so that the anchor comes in contact with the adhesive, and remove the remaining excess adhesive from therapy delivery element, a process which is generally time-consuming, messy, and could have an potential impact to the product performance should excess adhesive remain in undesirable locations.

In one embodiment, the fill port extends from a surface of the anchor to the space (e.g., a channel) for receiving the therapy delivery element. The fill port may include a threaded neck that engages threads of a neck of a tube of adhesive. The fill port may alternatively include some other type of connector for coupling to a dispenser for dispensing the adhesive. When the dispenser is coupled to the fill port in this manner, the adhesive may be dispensed into the fill port and introduced into the space containing the therapy delivery element. In this manner, the therapy delivery element is affixed to the anchor.

Fill port may be coupled, either removably or integrally, to a fill port extension. For example, this fill port extension may comprise a tube that extends from the fill port to some type of connector. This connector may be a luer hub or another type of connector that receives, or mates with, a dispenser for dispensing the adhesive. Use of the fill port extension allows the clinician to more readily dispense the adhesive into the fill port in a scenario wherein the anchor is positioned in a location that is hard to access. Since the second end may be sized to extend outside the body, the clinician is free to work unencumbered and may therefore more quickly complete the procedure.

A fill port may optionally extend into the space that receives the therapy delivery element from multiple side channels. Each such side channel may provide access to a different location of the space so that the adhesive may be introduced more uniformly. As one example, when the space is a main channel that is adapted to receive the therapy delivery element, the multiple side channels may extend to different points along the main channel so that adhesive may be dispensed along the length of the main channel.

In one embodiment, multiple fill ports may be provided. These multiple fill ports may be provided to introduce adhesive at various locations within the space. For instance, in an embodiment wherein the space is a main channel that receives a therapy delivery element, a first and a second fill port may be provided, each being located at a different end of the main channel. In another embodiment, a first and a second fill port may be provided on opposite sides of the main channel. Any of the fill ports may be provided with multiple channels extending to a different point of the main channel in the aforementioned manner.

One aspect of the disclosure relates to an anchor for securing a therapy delivery element in a desired location within a living body. The anchor includes an anchor body having a space to receive the therapy delivery element and a fill port provided in the anchor body to introduce an adhesive into the space when the therapy delivery element is positioned within the space.

A method according to this disclosure relates to securing a therapy delivery element within a living body. An anchor is provided that is adapted to receive the therapy delivery element. The anchor is positioned to receive the therapy delivery element. The anchor is provided with a fill port to transfer adhesive into a space between the anchor and the therapy delivery element. Adhesive is introduced into the space via the port so that the adhesive affixes the anchor to the therapy delivery element.

A system to deliver therapy to a living body is also disclosed. The system includes a therapy delivery device, a therapy delivery element extending from the therapy delivery device to deliver therapy to the living body, and an anchor to receive the therapy delivery element. A fill port extends from a surface of the anchor to a location where the anchor contacts the therapy delivery element. The fill port transfers adhesive to this location to affix the anchor to the therapy delivery element after the anchor has been situated in a selected position relative to the therapy delivery element.

According to another aspect, a system to deliver therapy to a living body is provided that includes an anchor to secure a therapy delivery element to the living body when the therapy delivery element is positioned in a selected manner relative to the anchor. A port in the anchor is provided to transfer adhesive to a space lying between an inner surface of the anchor and the therapy delivery element.

These and other aspects of the disclosure will become apparent to those skilled in the art from the following drawings and accompanying description.

BRIEF DESCRIPTION OF THE DRAWINGS

FIG. 8A is a top perspective view of another embodiment of an anchor.

FIG. 8B is a side view of an embodiment of a fill port extension having a threaded end that is adapted to mate with threads of an adhesive dispenser.

FIG. 8C is a side view of an embodiment of a fill port extension having a threaded end that is adapted to mate with a fill port.

FIG. 9 is a top view of an anchor that is similar to that shown in FIG. 8.

DETAILED DESCRIPTION OF THE PREFERRED EMBODIMENTS

Figure 1:
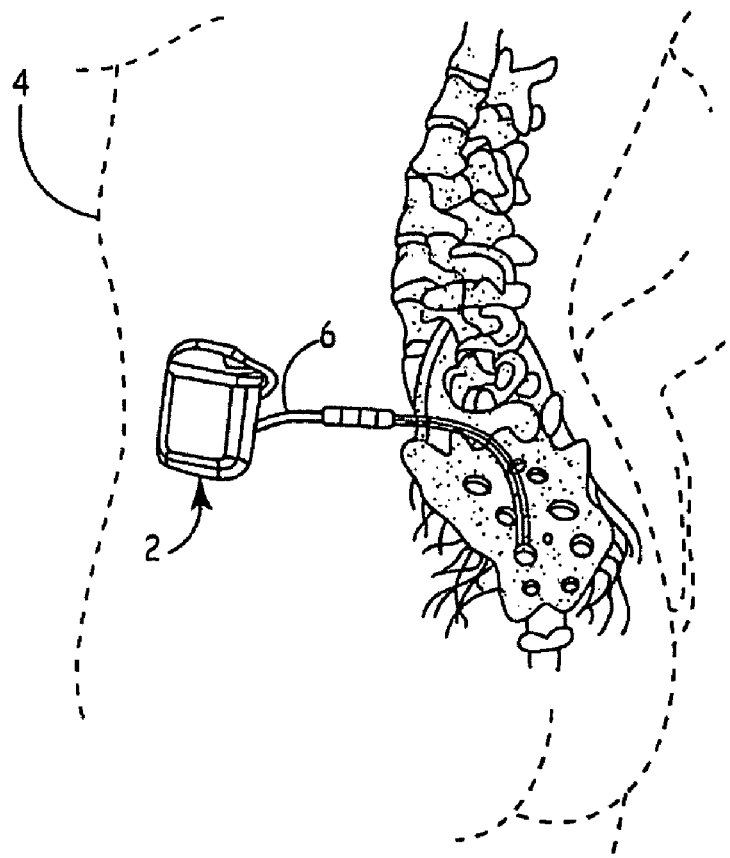
FIG. 1 is a system diagram showing a general environmental view that may benefit from use of an anchor according to the current disclosure.

FIG. 1 is a system diagram showing a general environmental that may benefit from use of an anchor according to the current disclosure. A therapy delivery device 2 is provided, which may be a stimulator for providing electrical stimulation, a device for delivering a substance, a system for delivering electrical stimulation and a substance, and/or a system for delivering any other type of therapy to patient 4. As an example, the therapy delivery device may be a neurostimulator, a pacemaker, a defibrillator, a drug delivery device including a pump, a microstimulator, or any other type of device for providing therapy to a living body.

Delivery of therapy may be performed by one or more therapy delivery elements 6. Such therapy delivery elements 6 may be leads, and/or catheters, or some other extension member of therapy delivery device that is needed to provide the therapy.

The therapy delivery device 2 is typically implanted subcutaneously in the body of patient 4 at a location selected by the clinician. The therapy delivery elements 6 are typically fixed in place near the location selected by the clinician using a device such as an anchor (not shown in FIG. 1). The anchor can be positioned on the therapy delivery element in a wide variety of locations and orientations to accommodate individual anatomical differences and the preferences of the clinician. The anchor may then be affixed to tissue in a variety of ways, such as by using one or more sutures, staples, screws, or other fixation devices. The tissue to which the anchor is affixed may include subcutaneous fascia layer, bone, or some other type of tissue. Securing the anchor to tissue in this manner prevents or reduces the chance that the therapy delivery element 6 will become dislodged or will migrate in an undesired manner.

Figure 2:
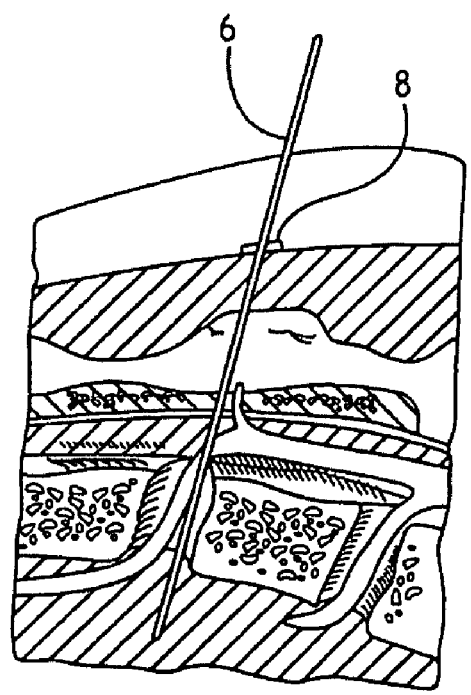
FIG. 2 is a cross-sectional view of tissue of a patient illustrating use of an anchor for securing a therapy delivery element.

FIG. 2 is a cross-sectional view of tissue of patient 4 illustrating use of an anchor 8 for securing a therapy delivery element 6. In this embodiment, anchor 8 is shown positioned in proximity to a dura layer. When affixed to this tissue, therapy delivery element 6, which in this case is a lead, is secured in a position to deliver a desired therapy regimen. Anchor 8 retains the therapy delivery element in the selected location so that efficacious therapy may be maintained.

As may be appreciated by FIG. 2, therapy delivery element 6 must be affixed to anchor 8 and anchor is, in turn, affixed to tissue or bone of patient 4. This prevents therapy delivery element 6 from migrating.

One way to affix therapy delivery element 6 to anchor 8 is by threading therapy delivery element 6 through an opening in the anchor. As discussed above, when anchor 8 is approximately at a desired location along a length of therapy delivery element 6, medical adhesive may be applied to the outer surface of therapy delivery element 6 at the target location that is to receive the anchor. The anchor 8 is then slid into this target location and into contact with the medical adhesive. Finally, the excess medical adhesive is removed from the outer surface of the therapy delivery element 6.

Fastening a therapy delivery element 6 to anchor 8 in the aforementioned manner may present challenges. For instance, first applying the adhesive, and then later removing the excess adhesive after the anchor is slid into position, may be difficult. This is particularly true when a small incision is being used to implant the therapy delivery element 6, or the therapy delivery device 2 is being implanted in a location that is difficult to access, leaving little room for the physician to work. These tasks increase the complexity of the procedure, and prolong the time required to complete the implant. These operations may further result in complications, as may occur when sliding the anchor into position causes displacement of some, or all, of the medical adhesive, leaving an insufficient amount of adhesive in proximity to the anchor to provide adequate fixation between the anchor 8 and the therapy delivery element 6.

The above-described concerns may be addressed by the use of one or more fill-ports that are provided in the anchor 8 to allow for infusion of medical adhesive into a space adjacent to both therapy delivery element 6 and anchor 8 after the anchor has been positioned in a desired location relative to therapy delivery element 6. Because an adequate amount of adhesive may be applied once the anchor is so positioned, better bonding results may be achieved. Moreover, because there is no need to slide the anchor into place after the adhesive is applied, excess adhesive need not be removed from therapy delivery element 6, a task that may be difficult, as discussed above.

Figure 3:
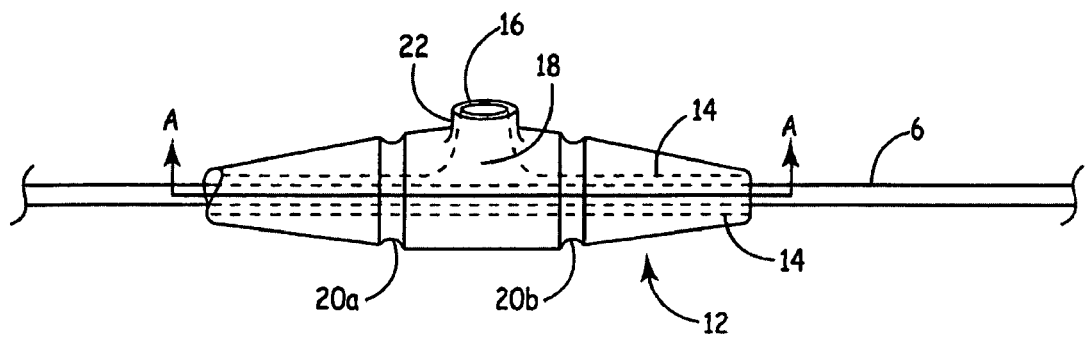
FIG. 3 is a side view of an exemplary anchor according to the current disclosure.

FIG. 3 is a side view of an exemplary anchor 12 according to the current disclosure. This anchor includes a space to receive the therapy delivery element 6, which in this embodiment is main channel 14 (shown dashed). A fill port 16 extends from a surface of the anchor into a port channel 18 (shown dashed) that accesses main channel 14. Medical adhesive that is injected into port channel 18 will be forced into the space in the main channel that surrounds therapy delivery element 6. This affixes therapy delivery element 6 to an inner surface of the anchor, which is this case is the inner surface of main channel 14, thereby maintaining the therapy delivery element at the desired location. Injection of the medical adhesive into port channel 18 may be accomplished in a variety of ways, as will be discussed below.

Anchor 12 of the exemplary embodiment includes grooves 20a and 20b. Surgical thread that is wrapped around anchor 12 at the location of the grooves may be secured to tissue or bone of a patient to retain anchor 12 at a desired location. The thread may also compress anchor 12 around therapy delivery element 6, thereby operating along with the medical adhesive to secure the anchor to therapy delivery element 6 at the desired location. Grooves 20a and 20b maintain the surgical thread at a location around anchor 12.

In addition to securing therapy delivery device 6 at a desired location, anchor 8 further helps add structure to therapy delivery element 6, making it easier to secure therapy delivery element to tissue. This is particularly helpful in the case of a therapy delivery element having an open lumen, such as a catheter. Such therapy delivery elements are more flexible, and for this reason may be harder to work with when attempting to position them at a desired location. When an anchor is provided around this type of therapy delivery element, the body of the anchor provides structure and stabilization, allowing the element to be more readily affixed to tissue.

Fill port 16 is shown to include a neck 22 that extends from a side surface of anchor 12. This neck may be provided to couple to a dispenser for dispensing medical adhesive in a manner to be discussed below. In an alternatively embodiment, this neck 22 may be eliminated such that fill port 16 is substantially flush with the side surface of anchor.

Figure 4:
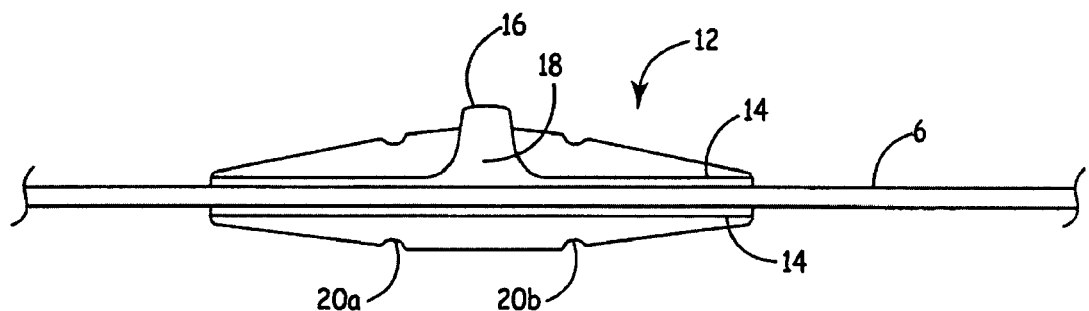
FIG. 4 is a cross-sectional view of an anchor along the plane indicated by line A-A of FIG. 3.

FIG. 4 is a cross-sectional view of anchor 12 along the plane indicated by line A-A. This cross-sectional view illustrates more readily port channel extending from port 16 to main channel 14. Therapy delivery element 6 is positioned within main channel 14, and will come in contact with medical adhesive injected into fill port 16.

Any type of biocompatible medical-grade adhesive may be employed with the anchor of the current disclosure. Such medical adhesive includes polyurethane and/or silicone adhesives. One example is Room Temperature Vulcanization (RTV) silicone adhesive which cures at room temperature. This type of adhesive is commercially available in tubes having a threaded neck similar to that shown and described below in reference to FIG. 6. This type of adhesive is generally kept under pressure to prevent it from curing at room temperature. When pressure is removed (e.g., the adhesive is dispensed from the tube) the adhesive will set up, becoming solid, or semi-solid in nature. Another example is a silicone or polyurethane adhesive that cures when exposed to UV or visible light, as is available from the Dymax Corporation.

Preferably, the selected adhesive has a viscosity that allows the adhesive to readily flow through port channel 18 and into main channel 14 so that the adhesive makes its way substantially to both ends of channel 14. This will provide for optimal adhesion between therapy delivery element 6 and anchor 12.

Figure 5:
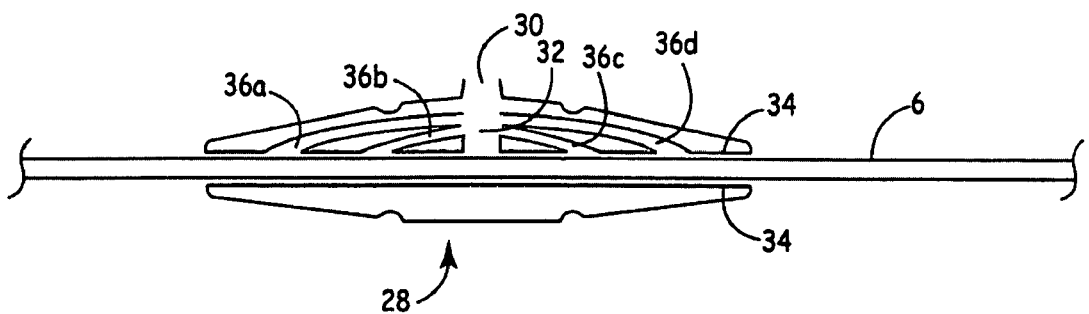
FIG. 5 is a cross-sectional view of another exemplary anchor according to the current disclosure.

FIG. 5 is a cross-sectional view of another exemplary anchor 28 according to the current disclosure. This cross-sectional view is provided along a similar plane, and illustrates similar elements, as FIG. 4. A fill port 30 leads to a port channel 32. A main channel 34 is provided to receive therapy delivery element 6. Side channels 36a, 36b, 36c, and 36d ("side channels 36") extend from port channel 32 into the main channel 34, providing additional pathways to carry the medical adhesive into the main channel. More or fewer side channels 36 than those shown may be provided. Additionally, these side channels need not reside in a same plane, but may fan out from fill port 30 in a spoke-and-hub fashion, extending throughout the circumference of anchor to provide still more paths to main channel 14. In this manner, the side channels allow adhesive introduced in fill port to reach different points along the main channel, thereby allowing for more uniform distribution of the adhesive within the main channel.

As discussed above, medical adhesive may be introduced into port channel 18, 30 of an anchor in a variety of ways. Several exemplary embodiments are provided in the following examples.

Figure 6:
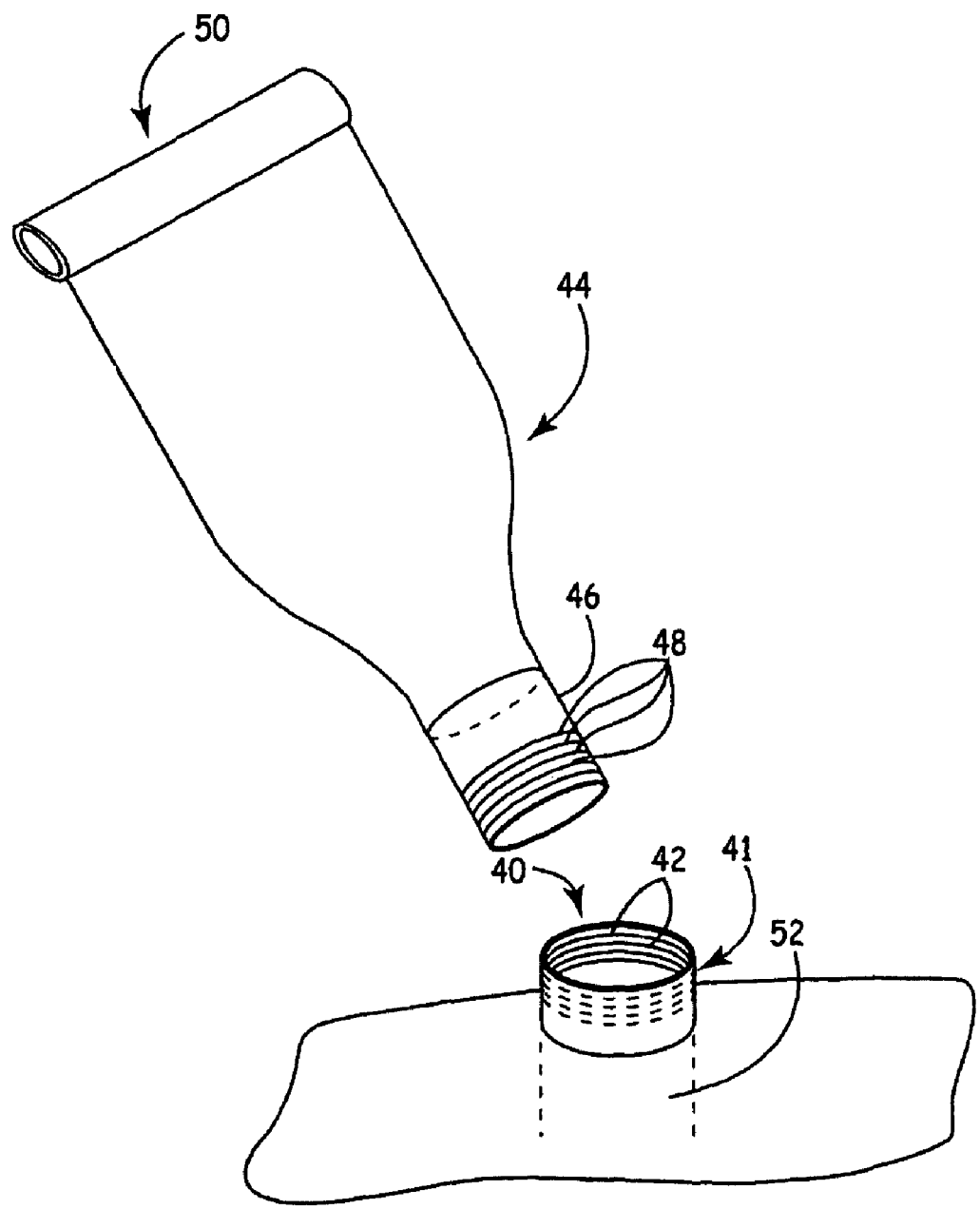
FIG. 6 is an exploded perspective view of a fill port that includes a threaded inner surface for mating with threads of a dispenser containing medical adhesive.

FIG. 6 is a detailed perspective view of a fill port 40 that includes a neck 41 having a threaded inner surface with threads 42. A tube 44 of medical adhesive includes a neck 46 with threads 48 on an outer surface. Threads 48 of neck 46 twist onto, and engage with, threads 42 of fill port 40. Once tube 44 of medical adhesive is secured to fill port 40 in this manner, pressure may be applied to tube 44, as by rolling tube 44 up from end 50. This injects medical adhesive from tube 44 into port channel 52 (shown dashed) in a manner similar to that described above. When an adequate amount of medical adhesive has been transferred into port channel 52 and from there into an associated main channel, tube 44 may be unscrewed from fill port 40 and the process is completed. If desired, fill port 40 may be provided with a cap that snaps or screws into position to seal fill port 40 while the medical adhesive cures.

Other embodiments are provided for connecting tube 44 to fill port 40. For instance, the circumference of an inner surface of neck 46 may be slightly bigger than outer surface of fill port 40. This inner surface of neck 46 may be provided with threads for engaging threads provided on an outer surface of fill port 40. In this embodiment, some medical adhesive may be deposited onto a portion of the outer surface of fill port 40 and may remain after tube is removed. This may require an additional step of wiping off the outer surface of fill port 40.

In yet another embodiment, outer surface of neck 46 of tube may have a relatively smooth surface. Similarly, inner surface of fill port 40 may likewise have a relatively smooth surface to slidably receive neck 46. An inner circumference of fill port may be sized only slightly larger than an outer circumference of neck 46 so that a snug fit results when neck is slidably inserted into fill port. This will prevent medical adhesive from flowing out of fill port 40 when pressure is applied to tube 44.

Other mechanisms may be provided to couple a dispenser of medical adhesive to a fill port. For instance, the dispenser may be provided with a connector that snaps into place on the fill port. As another example, a twist-lock mechanism of the type known in the art may be provided that allows a locking member on neck of the dispenser to be slid into place along of channel on the neck of fill port 40. The dispenser of adhesive may then be rotated relative to the fill port to allow the locking member of the dispenser to engage a locking lip of the fill port to secure the dispenser in position relative to the fill port. Many other types of connections may be utilized to couple a dispenser of adhesive to fill port 40 according to the current disclosure.

In yet another embodiment, neck 41 of fill port 40 may be eliminated. In this scenario, threads 42 may be provided within port channel 52 to engage threads 48 of tube 44. Alternatively, both the surface of port channel 52 and the neck 46 of tube 44 may be relatively smooth and sized to allow neck 46 to slidably engage port channel 52 to provide a snug fit.

Figure 7:
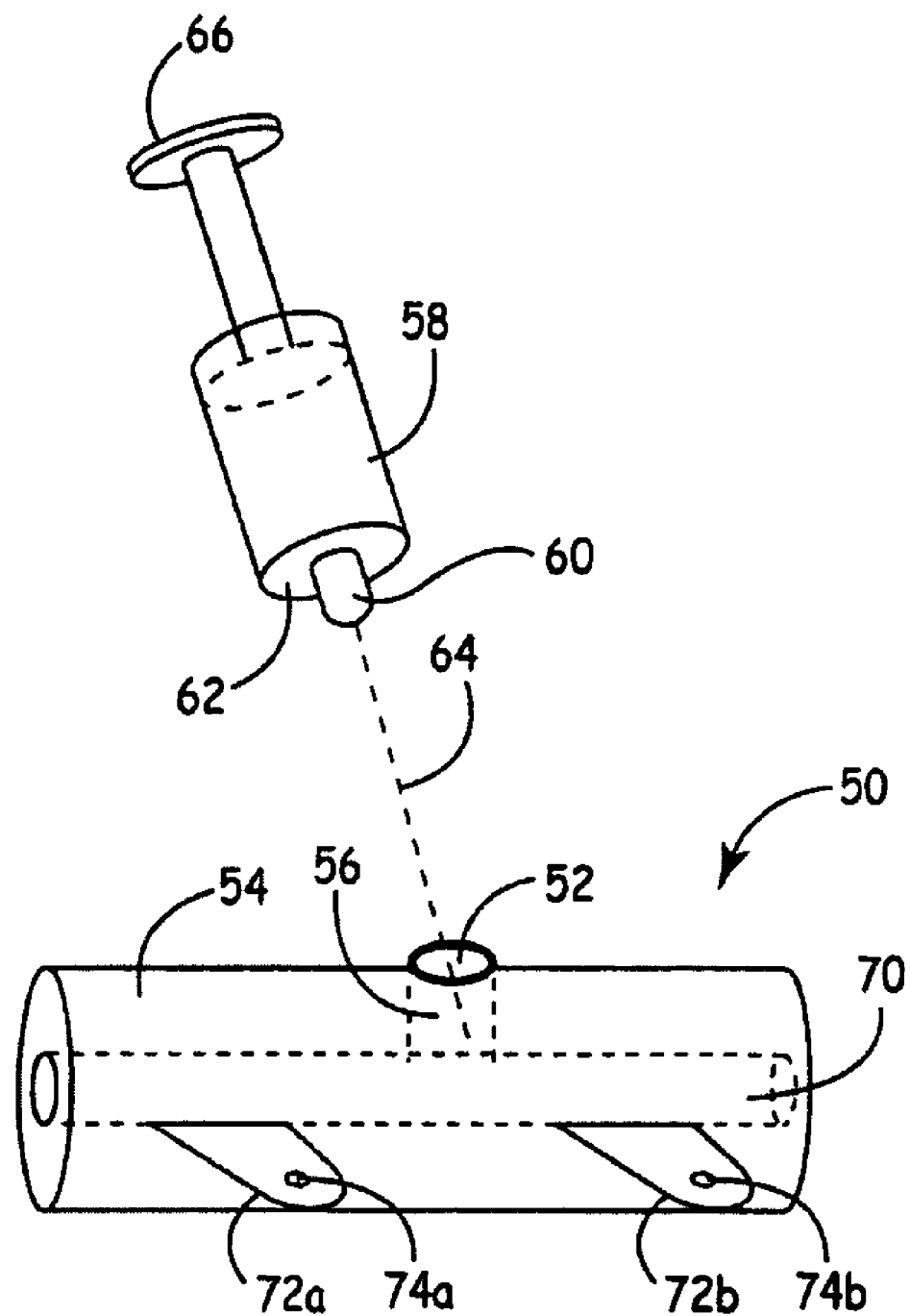
FIG. 7 is a perspective view of yet another embodiment of an anchor according to the current disclosure.

FIG. 7 is a perspective view of yet another embodiment of an anchor 50 according to the current disclosure. This embodiment provides a fill port 52 that is substantially flush with an external surface 54 of anchor 50. Fill port 52 provides entry into port channel 56 (shown dashed). A tube 58 containing medical adhesive includes a tip 60, which may be rounded. Tip 60 is designed to slidably engage, and provide a snug fit, with port channel 56. After tip is inserted into fill port 52 such that surface 62 of tube 58 is resting on external surface 54 of anchor 50, as indicated by dashed line 64, pressure is exerted on a plunger 66. This forces the medical adhesive into main channel 70 (shown dashed).

As was the case in the embodiments described above, tip 60 of tube 58 may couple to fill port 52 is other ways, as by including threads that may be screwed into complementary threads provided on an inner surface of port channel 56. Fill port 52 may be provided with a cap or other type of cover to seal the fill port after the medical adhesive has been injected into the main channel 70.

Anchor 50 further includes tabs 72a and 72b. Similar tabs (not shown) may be provided on an opposite side of anchor 50. Medical thread may be threaded through holes 74a and 74b, respectively, in tabs 72a and 72b and attached to tissue or bone of a patient to secure anchor 50 at a desired location with a body. Any of the embodiments described herein may employ such tabs 72a, 72b and/or grooves such as grooves 20a and 20b (FIG. 3) for use in securing an anchor at a location. Any of the anchor embodiments according to the current disclosure may alternatively or additionally include additional elements for securing the anchor to tissue or bone, such as eyelets that are provided directly in the anchor rather than in tabs for receiving medical thread, screws, staples or other affixing means for purposes of securing the anchor in a desired location.

FIG. 8A is a top perspective view of another embodiment of an anchor 80. This anchor includes grooves 82a, 82b, and tabs 84a, 84b for use in securing anchor 80 within a body. These elements are used in the manner described above with respect to grooves 20a, 20b (FIG. 3) and tabs 72a, 72b (FIG. 7). Anchor 80 includes a fill port 86 leading into a port channel (not shown), which further extends into a main channel 88 (shown dashed). Most notably, fill port 86 is coupled to a fill port extension 90. Fill port extension includes a first end 91 coupled to fill port 86, a second end 93 coupled to a connector shown to be a luer-style connector 92. Such a connector may include a luer hub or a luer stub, for instance. An intermediate portion 94 extends between first end 91 and second end 93. Fill port extension 90 may be formed of medical grade tubing such as a silicone or polyurethane tubing.

Luer-style connector 92 and fill port extension 90 may receive a syringe 94 filled with medical adhesive. Depressing plunger 96 of syringe 94 forces the medical adhesive through fill port extension 90 into port channel, and further into main channel 88 to affix a medical therapy element positioned within main channel 88 to anchor 80. In another scenario, syringe 94 may be used to introduce medical adhesive into only a portion of second end 93. A pneumatic system may then be used to inject a short burst of compressed gas (e.g., air) into the second end 93 to force the injected adhesive into main channel 88 around the medical therapy element that is located within this channel.

Other types of connections may be provided instead of luer-style connector 92 at the second end 93 of fill port extension 90. For instance, FIG. 8B is a side view of fill port extension 90A. In this embodiment, second end 93B of a fill port extension 90A includes a neck with threads to twist onto, and connect with, the threads of a dispenser that contains medical adhesive, such as tube 44 of FIG. 6. The threads may be either on an outer surface or an inner surface of the neck. Any other type of connector may be provided in the alternative.

In either of the embodiments shown in FIGS. 8A and 8B, fill port extension 90 or 90A may be integrally coupled to fill port 86 via a first end. In another embodiment, fill port extension 90 or 90A may be removably coupled to fill port 86, as discussed in relation to FIG. 8C.

FIG. 8C illustrates a first end 100 of fill port extension 90B. This type of end may be provided as first end 91 of fill port extension 90 of FIG. 8A, and/or may be provided as a first end of fill port extension 90A of FIG. 8B. First end 100 includes threads 101 to twist onto, and receive, complementary threads that are provided in an inner surface of a port channel such as port channel 52 of FIG. 7. This allows a fill port extension to be selectably coupled to a port channel in those situations where this type of extension is needed, as when location or depth of implant, rotation of the anchor within a body, and/or encroachment of tissue around anchor after initial anchor placement may make it difficult for a physician to access a fill port directly to dispense medical adhesive into port channel. In addition, use of fill port extension 90A may allow medical adhesive to remain outside of the sterile zone of a patient, thereby simplifying the procedure. Fill port extension 90A need not be coupled to a fill port in other situations wherein adhesive may be readily introduced directly into the fill port without difficulty.

Other types of connection mechanisms other than threads may be provided at a first end of a fill port extension for coupling the fill port extension to a fill port in this manner. For instance, a snap-fit connection and a twist-and-lock mechanism are some additional examples that may be used at a first end of fill port extension for removably coupling the fill port extension to a fill port.

Once medical adhesive is dispensed via fill port extension 90 or 90A, this appendage may be removed, as by cutting it off. For instance, if fill port extension 90 is implemented as tubing, the tubing may be clipped off at fill port 86. Alternatively, fill port extension may be clipped off somewhere along the intermediate portion between the first end 91 and second end 93 of the fill port extension, as may be necessary if it is difficult to access the first end of the fill port extension located at fill port 86. In either case, it may be advantageous to tie a knot in the fill port extension prior to removing the remainder of the fill port extension (e.g., as by cutting it off) so that adhesive will not be discharged in an unwanted manner from the clipped end prior to the curing of the adhesive.

FIG. 9 is a top view of an anchor 103 that is similar to that shown in FIG. 8. This embodiment includes grooves 102*a*, 102*b* of the type discussed above. Also provided are two fill ports 104*a* and 104*b* located at opposite ends of main channel 106 (shown dashed). Each fill port includes a fill port extension 108*a* and 108*b*, respectively, which may be of the type described in regards to FIG. 8. Use of two fill ports 104*a* and 104*b* may allow medical adhesive to be more uniformly distributed throughout main channel 106, and may further allow the medical adhesive to be infused within channel using a lower pressure.

Figure 10:
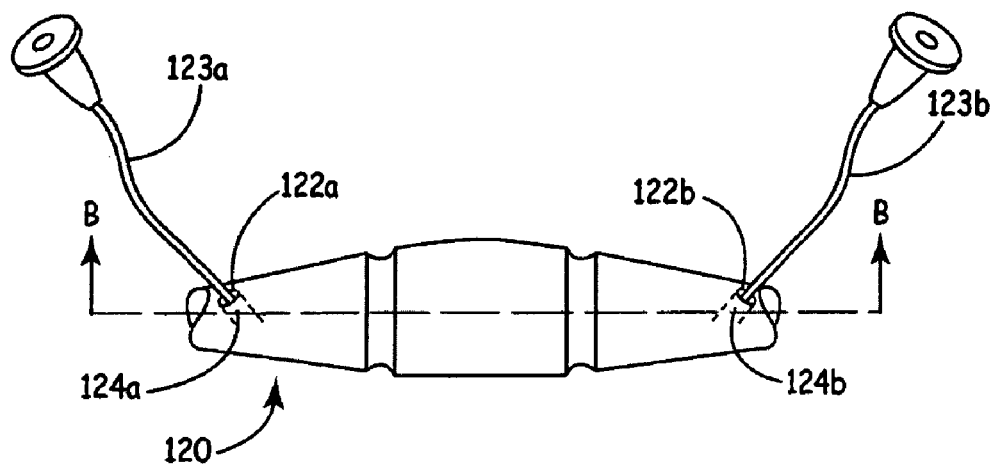
FIG. 10 is a side view of an embodiment of an anchor that includes two fill ports at opposite ends of a main channel of the anchor.

FIG. 10 is a side view of an embodiment of an anchor 120 that includes two fill ports 122*a* and 122*b*. In this instance, fill ports 122*a* and 122*b* are located at opposite ends of anchor 120, each extending into a respective port channel 124*a* and 124*b* (shown dashed) that may be angled relative to a main channel (not shown in FIG. 10). As was the case with the embodiment of FIG. 9, providing fill ports at either end of anchor may allow medical adhesive to be more uniformly distributed into the main channel.

As may be appreciated, any number of fill ports may be provided for any of the embodiments disclosed herein. These ports may be provided anywhere on anchor that may be accessible to the physician. In one embodiment, fill ports may be provided at locations around the circumference of anchor, with the physician deciding which fill port to utilize after the anchor is in position, and it is evident which fill port is most easily accessed.

In the instant case, both of fill ports 122*a* and 122*b* are provided with fill port extensions 123*a* and 123*b*. However, this need not be the case. Any one or more of fill ports 122*a* and 122*b* may be provided within a fill port extension. In an embodiment wherein fill ports are provided that may not necessarily be used in the procedure, it may not be desirable to provide fill port extensions. This may be the case, for instance, when fill ports are provided around the circumference of anchor 120 such that some fill ports will invariably be inaccessible to the physician when the anchor is within a body.

Figure 11:
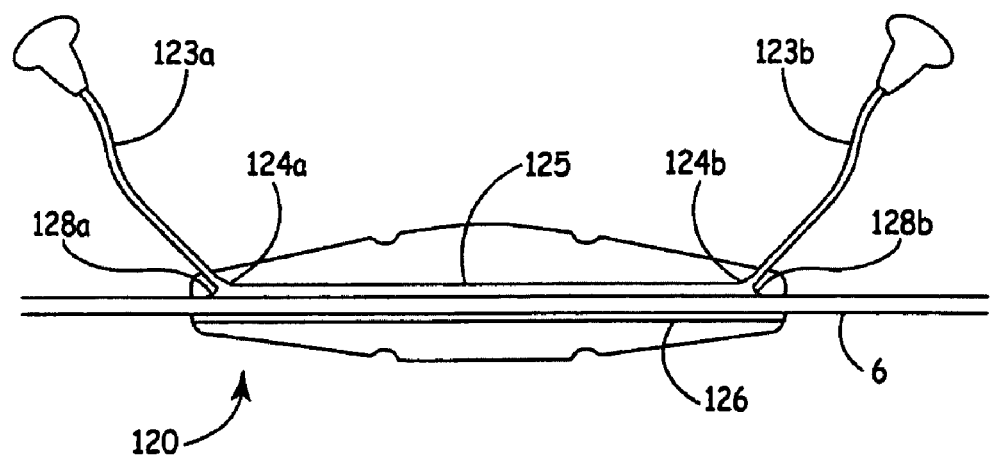
FIG. 11 is a cross-sectional view of the anchor of FIG. 10 along line B-B of FIG. 10.

FIG. 11 is a cross-sectional view of anchor 120 in a plane defined by line B-B of FIG. 10. This view illustrates angled port channels 124*a* and 124*b* that extend into an enlarged portion 125 of main channel 126. When therapy delivery element 6 lies within main channel 126, therapy delivery element is maintained in this position by openings 128*a* and 128*b* at either end of main channel 126. This positioning of therapy delivery element 6 leaves enlarged portion 125 unobstructed to receive medical adhesive that is introduced via port channels 124*a* and 124*b*. This embodiment may therefore allow the adhesive to be readily introduced into main channel 126 at a lower pressure and in a uniform way.

Figure 12:
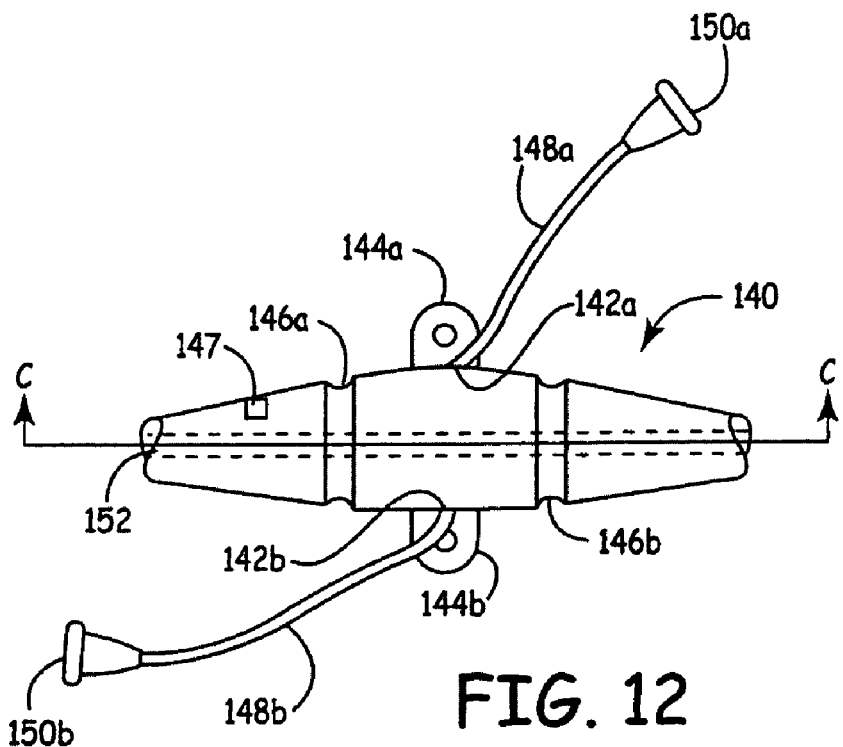
FIG. 12 is a side view of an embodiment of an anchor that includes two fill ports at opposite sides of the anchor.

FIG. 12 is a top view of another anchor 140 that includes two fill ports 142*a* and 142*b* on opposite sides of the anchor and further on opposite sides of a main channel 152 (shown dashed). Anchor 140 further includes two tabs 144*a* and 144*b*, also on opposite sides of the anchor, as well as grooves 146*a* and 146*b*. Tabs 144*a*, 144*b* and/or grooves 146*a*, 146*b* may be eliminated in another embodiment. Alternatively, more or fewer tabs and/or grooves may be provided.

Each of fill ports 142*a* and 142*b* extend into a fill port extension 148*a* and 148*b*, respectively. These fill port extensions each terminate in a respective luer hub 150*a* and 150*b*, although another type of connector may be provided in the alternative.

Anchor 140 may be positioned within a patient such that both fill port extensions 148*a* and 148*b* extend from the body. Each such fill port is adapted to mate with a dispenser (e.g., a syringe, tube, etc.) containing medical adhesive so that the adhesive may be introduced into a respective port channel (not shown in FIG. 12) located on opposite sides of main channel 152. This allows the adhesive to bond to both sides of a therapy delivery element that is located within main channel, thereby providing additional fixation capabilities.

In one embodiment, anchor 140, or any of the other embodiments of anchors shown or described herein, may include an RFID tag 147. Such a tag may include an antenna adapted to passively provide information when an electromagnetic waveform is generated in the vicinity of anchor 140 by an RFID reader. This tag may be used to identify the anchor after implant. The tag may provide information such as the type of anchor, type of adhesive employed with anchor, type of therapy delivery element used with the anchor, and so on. If desired, the chip may store patient-specific information.

Alternatively or additionally, radio-opaque marker may be provided in a portion of anchor 140 to allow the anchor to be visible on X-rays or other forms of radiation imaging.

Figure 13:
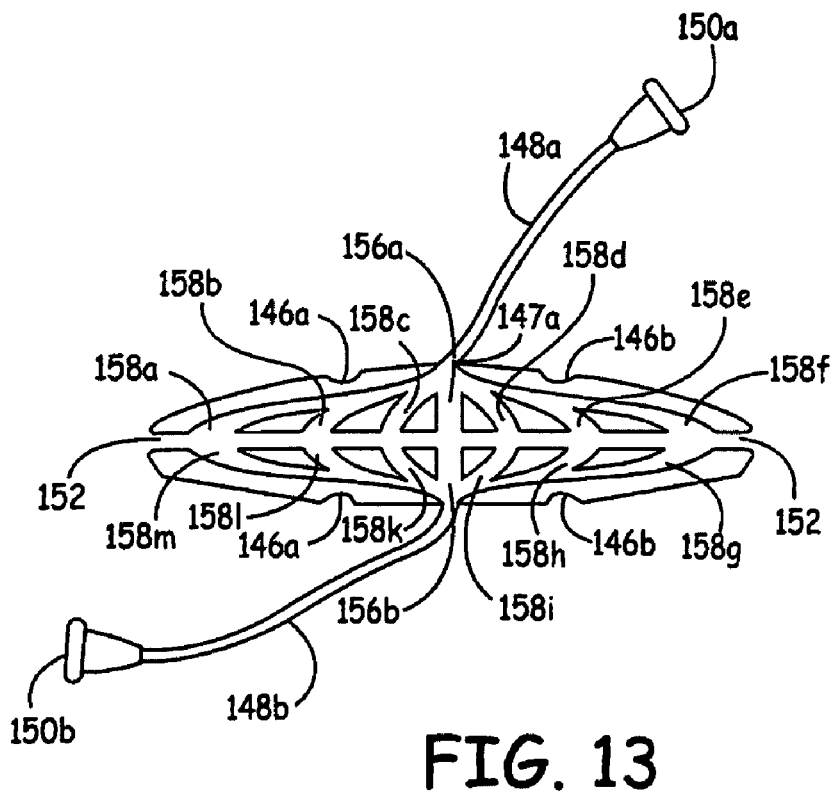
FIG. 13 is a cross-sectional view of the anchor of FIG. 12 along line C-C of FIG. 12.

FIG. 13 is a cross-section view of anchor 140 along a plane defined by line C-C of FIG. 12. In this view, it is assumed that tabs 144*a*, 144*b* of FIG. 12 are proximate to, but not co-planar with, fill ports 142*a*, 142*b*, respectively, and thus are not shown in this drawing.

FIG. 13 illustrates fill ports 142*a* and 142*b* extending into port channels 156*a* and 156*b*, respectively, which are located on opposite sides of a main channel 152. Each of port channels is shown extending into optional side channels 158*a*-158*m*. More or fewer side channels may be provided in another embodiment, or the side channels may be eliminated altogether. Use of these optional side channels may allow the medical adhesive to be more evenly dispersed throughout main channel 152. It will be understood that not all such side channels need be co-planar in the manner shown in FIG. 13. For instance, side channels may extend radially from each fill port in a hub-and-spoke type configuration.

When tabs are provided on same sides as anchor 140 as the fill ports 142*a*, 142*b* in the manner shown in FIG. 12, anchor 140 will generally be positioned within a body so that the fill ports appear on either side of the anchor. In another embodiment, tabs 144*a*, 144*b* and fill ports 142*a*, 142*b* may be offset from one another by 90 degrees around the circumference of the anchor body. In this case, when the anchor is positioned within a body such that tabs 144*a*, 144*b* are located on either side of the anchor, one fill port is extending generally upward and the other fill port is extending downward into the body. In this scenario, the downward-extending fill port is not directly accessible to a physician, but can never-the-less be employed to introduce medical adhesive so long as a fill port extension is provided that is sized to extend from the body even when the associated fill port is inaccessible in this manner. In this case, at least some portion of the fill port extension will remain in the body after the procedure is complete since the physician will be unable to cut the entire fill port extension from the fill port since the fill port is not accessible.

As discussed above, the current system and methods may be practiced using any type of medical-grade adhesive. Many such adhesives are formed of bio-compatible silicone. This type of silicone may not adhere in an optimal manner to therapy delivery elements or anchors made of polyurethane or other non-silicone materials. Similarly, if a polyurethane adhesive is used, the adhesive may not bond in an optimal way to a therapy delivery element or an anchor that is formed of something other than polyurethane. To address the foregoing challenge, enhancing the ability of adhesive to bond to a therapy delivery element that is made of a different material, a therapy delivery element may be provided with one or more anchor zones. Such anchor zones may be formed using a material that is the same as, or similar to, the adhesive. For instance, if a silicone adhesive is being employed, the anchor zones may be formed of silicone.

Figure 14:
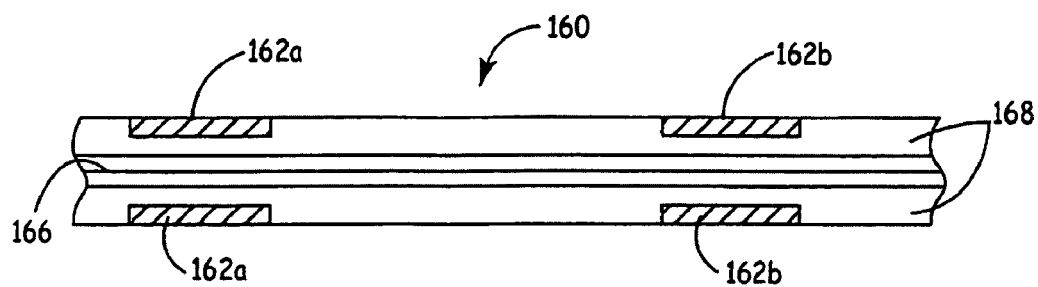
FIG. 14 is a cross-sectional view of a lead having anchor zones for receiving an anchor.

FIG. 14 is a cross-sectional view of a lead 160 having anchor zones 162a and 162b, which for this example, will be described as being formed of silicone. Lead 160 includes a lumen 164 that houses at least one conductor 166. Jacket 168 of lead 160 may be formed of polyurethane or some other non-silicone biocompatible material. Anchor zones 162a and 162b (shown hashed) are formed by removing predetermined portions of jacket 168, and replacing these removed portions with silicone or some other material that optimally adheres with silicone medical adhesive. For instance, the portions may be removed using a chemical or laser etching process. Silicone may then be added to the removed portion using an over-molding process. Alternatively, silicone adhesive such as RTV silicone may be deposited into the removed portion in a manner that provides the therapy delivery device with a smooth outer profile and then allowed to cure.

The anchor zones may be of a different color than the rest of jacket 168 so that a physician can readily identify, and optimally position, an anchor at one of these zones. Multiple anchor zones may be provided at various positions along the length of lead 160 to allow a physician to select an anchor zone that is most optimal for positioning an anchor based on an individual patient, the type of therapy delivery device in use, and the procedure that is being performed. Anchor zones 162a and 162b may be longer than the length of an anchor so that the anchor may be selectively positioned anywhere along the length of the anchor zone. Alternatively, the anchor zones may be the same size as, or smaller than, an anchor that will be used with catheter 180.

Anchor zones may extend around an entire circumference of a therapy delivery device (e.g., anchor zone 162a and 162a may be a single anchor zone extending around body of lead 160), or alternatively, anchor zones may include discontinuous segments around the circumference of a therapy delivery element.

Figure 15A:
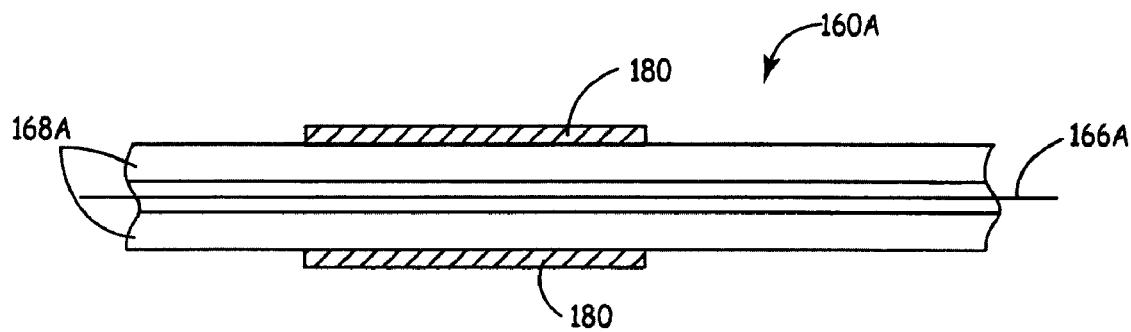
FIG. 15A is a cross-sectional view of a lead having an anchor zone that is not co-extensive with the rest of the lead body.

FIG. 15A is a cross-section view of a lead 160A having an anchor zone 180 (shown hashed) provided over a portion of jacket 168A. For instance, anchor zone 180 could be formed of a heat-shrink silicone tubing that is slipped into place over jacket 168A and then form-fitted by applying heat. The silicone could alternatively be deposited using an over-molding process. In this case, anchor zone 180 has a profile that is slightly raised as compared to anchor zones 162a and 162b of FIG. 14, which have a surface that is substantially co-extensive with jacket 168.

Anchor zone 180 may be part of a single anchor zone that extends around the 5 circumference of lead 160A, or may be two of multiple discrete segments positioned around the circumference of lead 160A.

Figure 15B:
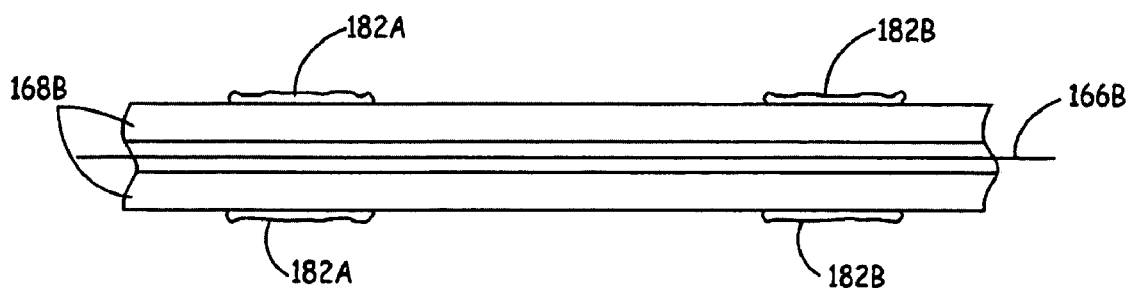
FIG. 15B is a cross-sectional view of a lead having anchor zones that are provided with a rough surface to increase ability to bond with adhesive.

FIG. 15B is yet another embodiment of a lead 160B having anchor zones 182A and 182B that are formed by depositing silicone on jacket 168B using a sputtering process so that the anchor zones have a more rough surface than is provided by jacket 168B.

While all of the anchor zones of FIGS. 14, 15A, and 15B are described in reference to leads, similar anchor zones may be provided on other therapy delivery elements such as catheters. Moreover, although the anchor zones are describes as being formed of silicone deposited on a non-silicone jacket, the anchor zones may instead be formed of polyurethane deposited on a jacket made of a material that is other than polyurethane. Other combinations of materials may be used. Typically, the anchor zone will be formed of a material that will form a good bond with the adhesive that is intended for use in securing the anchor.

In the above-discussed embodiments of lead anchors, all anchors are described and shown as having a space, such as a main channel, that slidably receives a therapy delivery element that is inserted into the space, as by threading the therapy delivery element through the space (e.g., channel). This need not be the case. Other embodiments of the disclosed anchor may have a space that is accessed by opening, or otherwise exposing this space, so that the therapy delivery element may be placed inside the space without using a threading-type operation. This is shown and described in reference to FIG. 16.

Figure 16:
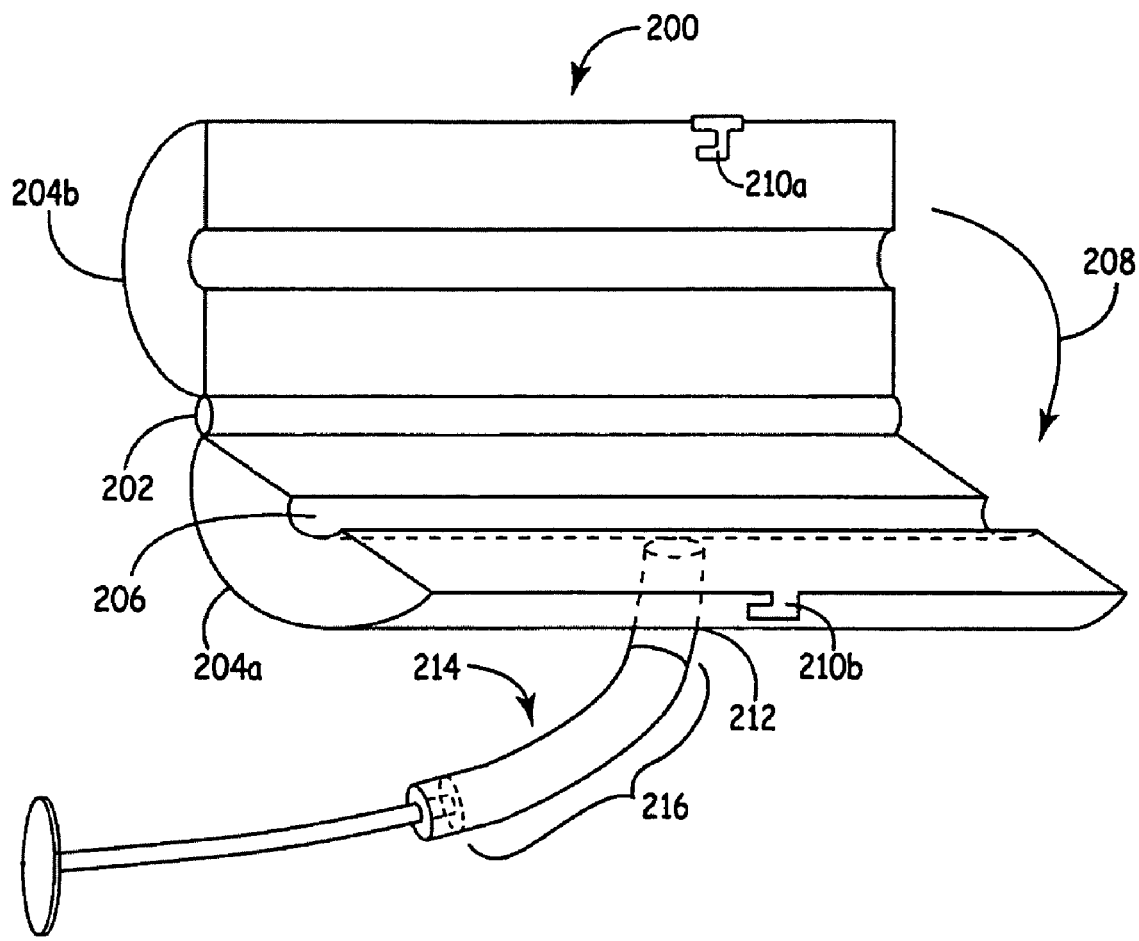
FIG. 16 is a side perspective view of another embodiment of an anchor according to the current disclosure.

FIG. 16 is a side perspective view of another embodiment of an anchor 200 according to the current disclosure. Anchor 200 includes a hinge 202 that connects two portions 204a and 204b of the anchor 200. Both portions are provided with a portion of a space for receiving a therapy delivery device (not shown). In this instance, the space comprises a main channel 206 that is exposed when the two portions 204a and 204b of the anchor are separated in the manner shown in FIG. 16. After a therapy delivery element is positioned within main channel 206 of one of the two portions 204a or 204b, the two portions are positioned next to one another, as indicated by arrow 208. The two portions 204a and 204b may be maintained in this closed position by any type of a clasping mechanism such as a slidable hook 210a and an engaging eye mechanism 210b.

Next, the anchor may be slid along a length of the therapy delivery device to a desired location, at which point the anchor may be secured by introducing medical adhesive into main channel 206 via port 212. In the example embodiment, this is accomplished using fill port extension 214.

It may be noted that in the embodiment of FIG. 16, the ability to open the two portions 204a and 204b of anchor 200 to expose main channel 206 would allow medical adhesive to be readily introduced directly into main channel 206 without use of fill port 212. However, it may never-the-less be advantageous to include a fill port in this type of embodiment because this will allow anchor 200 to be maintained in a secure position surrounding a therapy delivery element once the anchor has been positioned within a body. When the anchor is so positioned, opening portions 204a and 204b to introduce the medical adhesive would provide opportunity for the anchor to become separated from a therapy delivery device, causing undue delay in completely the procedure. Use of the fill port 212 prevents this type of occurrence.

In one embodiment, a fill port extension may comprise a tube that has been pre-loaded with a predetermined amount of medical adhesive. In one embodiment, to prevent this pre-loaded medical adhesive from curing at room temperature, it must be maintained under pressure until the time the anchor is to be deployed. In another embodiment, the pre-loaded medical adhesive is UV or visible-light curable. In this latter case, the adhesive is kept from exposure to UV or visible light until the time of anchor deployment, at which time a device that emits the required electromagnetic waves is used to promote the curing of the adhesive.

Figure 17:
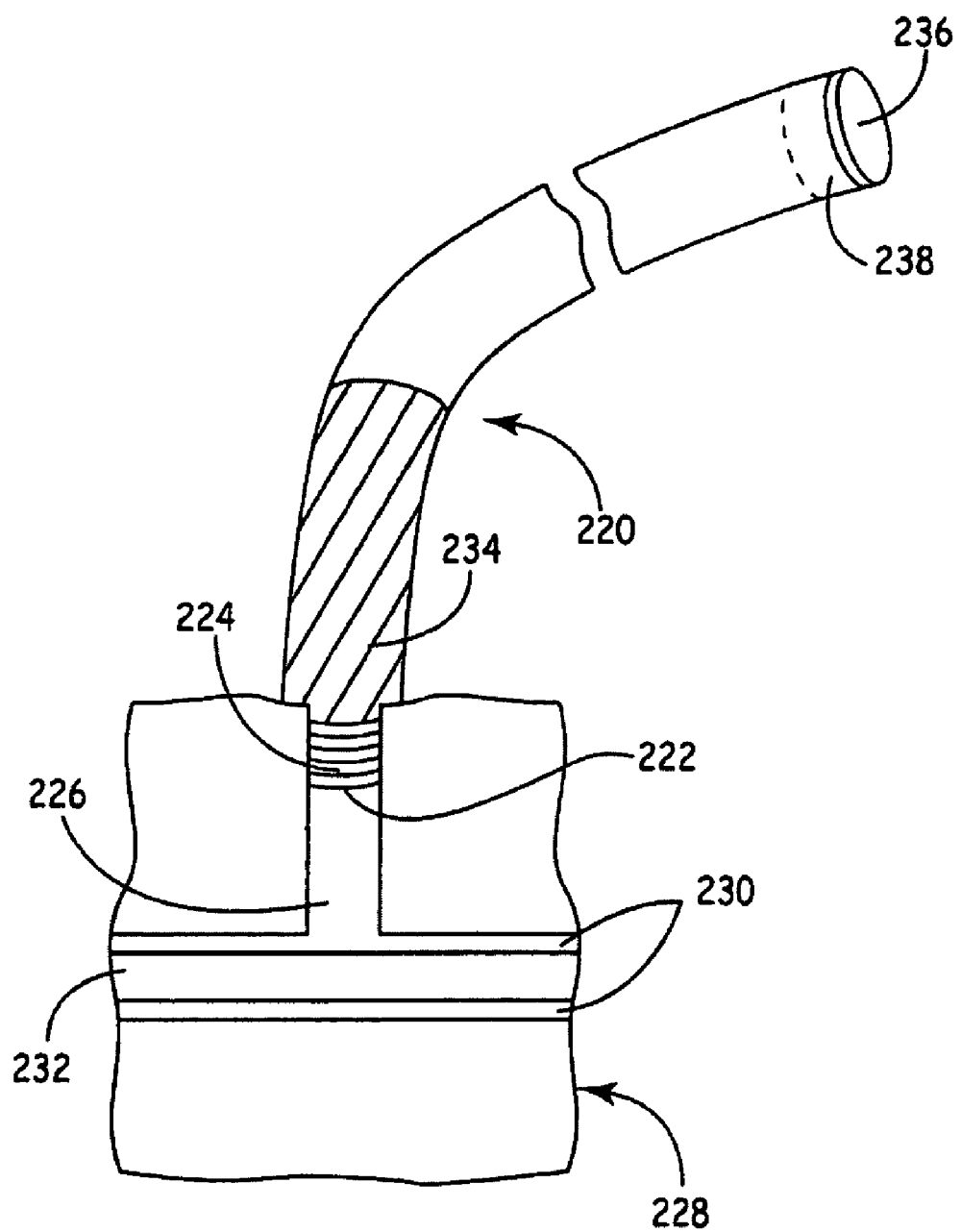
FIG. 17 is a cross-sectional view of a fill port extension that has been pre-loaded with medical adhesive.

FIG. 17 is a cross-sectional view of a fill port extension 220 having a first end 222 that includes a neck 224. This neck is shown inserted into a port channel 226 of anchor 228 (only a portion of which is shown). Neck 224 may include threads that mate with threads within port channel 226. Alternatively, neck 224 may slidably engage with channel 226 to form a snug fit. In another embodiment, the fill port extension 220 may be integrally formed with the fill port.

Port channel 226 extends into main channel 230 of anchor 228 in which a therapy delivery element 232 may be positioned. During a manufacturing process, and prior to use, first end 222 of fill port extension 220 is preloaded with a predetermined amount of adhesive 234 (shown hashed). The adhesive may be pressurized to prevent adhesive 234 from curing at room temperature. Alternatively, the adhesive may be UV or visible-light curable. A cap 236 or other covering may be provided at end 238, and a similar cap may be provided to cover end 222 (not shown in FIG. 17). These caps may be tear-away covers such as provided by foil, may be pressure-fit plugs similar to corks, may be threaded caps that engage matching threads of fill port extension, or any other type of cover. In the case wherein the adhesive cures upon being de-pressurized, the cap maintains pressure within fill port extension so that adhesive 234 will not cure at room temperature.

At the time anchor 228 is to be deployed, the cap may be removed from end 222 so that neck 224 may be coupled to port channel 226, as by being screwed into place in the manner shown in FIG. 17. Cap 236 may also be removed from end 238. A pneumatic system may be fitted to end 236 to provide a small burst of gas (e.g., air) to eject adhesive from end 222 of fill port extension 220 and introduce the adhesive from port channel 226 into main channel 230 surrounding therapy delivery device 232. Pneumatic system may be a pump that delivers pressurized gas. Alternatively, it may be a manual system such as a plunger that has a form fit with end 238 to prevent gas from escaping at end 238 when the plunger is deployed, and which thereby ejects adhesive 234 from end 222. If the adhesive is of a type that is cured by exposure to electromagnetic waves, the appropriate waves (e.g., UV waves or visible light) are provided, as via a light wand that is positioned within port channel 226.

Figure 18:
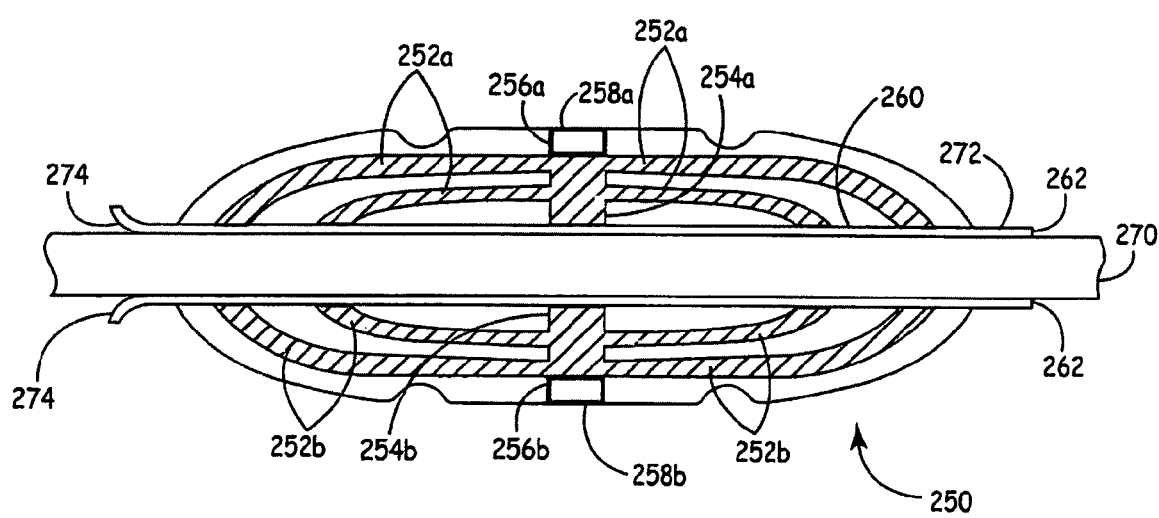
FIG. 18 is a cross-sectional view of an anchor that has channels pre-loaded with adhesive.

In a manner similar to the foregoing, adhesive may likewise be pre-loaded into channels of an anchor, as is shown in regards to FIG. 18.

FIG. 18 is a cross-sectional view of an anchor 250 that has side channels 252a and 252b that have been pre-loaded with adhesive (shown hashed). In this embodiment, side channels 252a extend from port channel 254a, and side channels 252b extend from port channel 254b. Port channels 254a and 254b ("port channels 254") extends to a surface of anchor 250 through fill ports 256a and 256b, which are shown covered via caps 258a and 258b.

Side channels 252a and 252b ("side channels 252") and port channels 254 extend to a main channel 260 adapted to receive a therapy delivery element in the manner described above. At the time of manufacture, a tubular retention member 262 is positioned within this main channel 260. This retention member 262 is maintained within main channel 260 until the time anchor is deployed to prevent the adhesive which has been pre-loaded into side channels 252 and port channels 254 from flowing into main channel 260. In the case wherein adhesive is of a type that cures at room temperature when depressurized, retention member 262 further maintains adhesive under pressure so that it does not cure at room temperature.

In one example, anchor 250 is manufactured as follows. A mandrel is threaded through the middle of retention member 262 so that the retention member may be more readily handled. Retention member 262 may be formed of a stainless steel tube, a tube formed of MP35N nickel-cobalt alloy, or a tube formed of another alloy that will provide a suitable hoop strength. The walls of retention member are preferably as thin as possible while still having the hoop strength to withstand pressure that will be exerted upon retention member by the inner surface of main channel 260 of anchor 250, as well as the pressurized adhesive that will be introduced within side channels 252 and port channels 254. When using MP35N, the walls of retention member may on the order of between 1 and 0.1 mils thick, for example.

After retention member is positioned on a mandrel, an injection molding process is used to inject silicone or polyurethane into a mold to form an anchor such as that shown in FIG. 18 that surrounds retention member 262. The injection molding process may be completed in multiple steps, if desired. Next, adhesive is introduced under pressure into side channels 252 and port channels 254 of anchor 250. As discussed above, adhesive will not enter main channel 260 because of the presence of retention member 262 within main channel 260. Caps 258a and 258b are inserted or otherwise coupled to cover fill ports 256a and 256b, respectively, and maintain adhesive under pressure, if necessary. Caps may be pressure-fit plugs similar to corks, may be threaded caps that engage matching threads of fill port extension, or any other type of cover that maintains any necessary pressure within port channels 254 and side channels 252. In one embodiment, caps 258a and 258b are configured so that when covering fill ports 256a and 256b, anchor 250 has a smooth side profile, as shown in FIG. 18.

During use, a therapy delivery element 270 is threaded through retention member 262 so that anchor 250 is positioned at approximately a desired position along the length of therapy delivery element 270. A clinician grasps one side of retention member 262 (e.g., side 272) and exerts force to slide anchor 250 off of retention member 262 and directly onto body of therapy delivery element 270. In one embodiment, retention member 262 may include a lip 274 or some other structure to allow the clinician to more readily grasp retention member 262 and apply sideways pressure to slide anchor 250 from the retention member. The removal of anchor 250 from retention member 262 is possible because the stainless steel, MP35N or other alloy used to form retention member 262 has a non-stick coating such as medical-grade Teflon® that does not adhere to the silicone or polyurethane used to mold the body of anchor 250.

As anchor 250 is slid from retention member 262, elasticity of the anchor 250 provided by the polyurethane or silicone with which the anchor is formed causes main channel 260 to contract slightly around therapy delivery element 270 to help hold anchor 250 at the desired position along the length of therapy delivery element. Also at this time, this operation releases pressure from side channels 252 and main channel 254, causing adhesive to flow into main channel 260 around therapy delivery element 270. If the adhesive is of a type that cures at room temperature upon release of pressure, this operation will allow the adhesive to set, holding anchor in position. If the adhesive is curable upon exposure to electromagnetic waves, the appropriate waves are supplied, as by positioning a light wand in proximity to one or both ends of main channel 254.

It will be appreciated the embodiment of FIG. 18 is merely exemplary, and such an embodiment may include more or fewer side channels 252, fewer fill ports 256, the anchor body may be configured in another shape, and so on. Moreover, caps 256a and 256b need not provide a smooth profile. Thus, it is understood many embodiments are possible within the scope of the disclosure. Such embodiments provide a mechanism wherein anchor 250 is pre-loaded with adhesive via fill ports 256a and 256b prior to use so that the clinician may eliminate the step of introducing the adhesive during an implant procedure.

Figure 19:
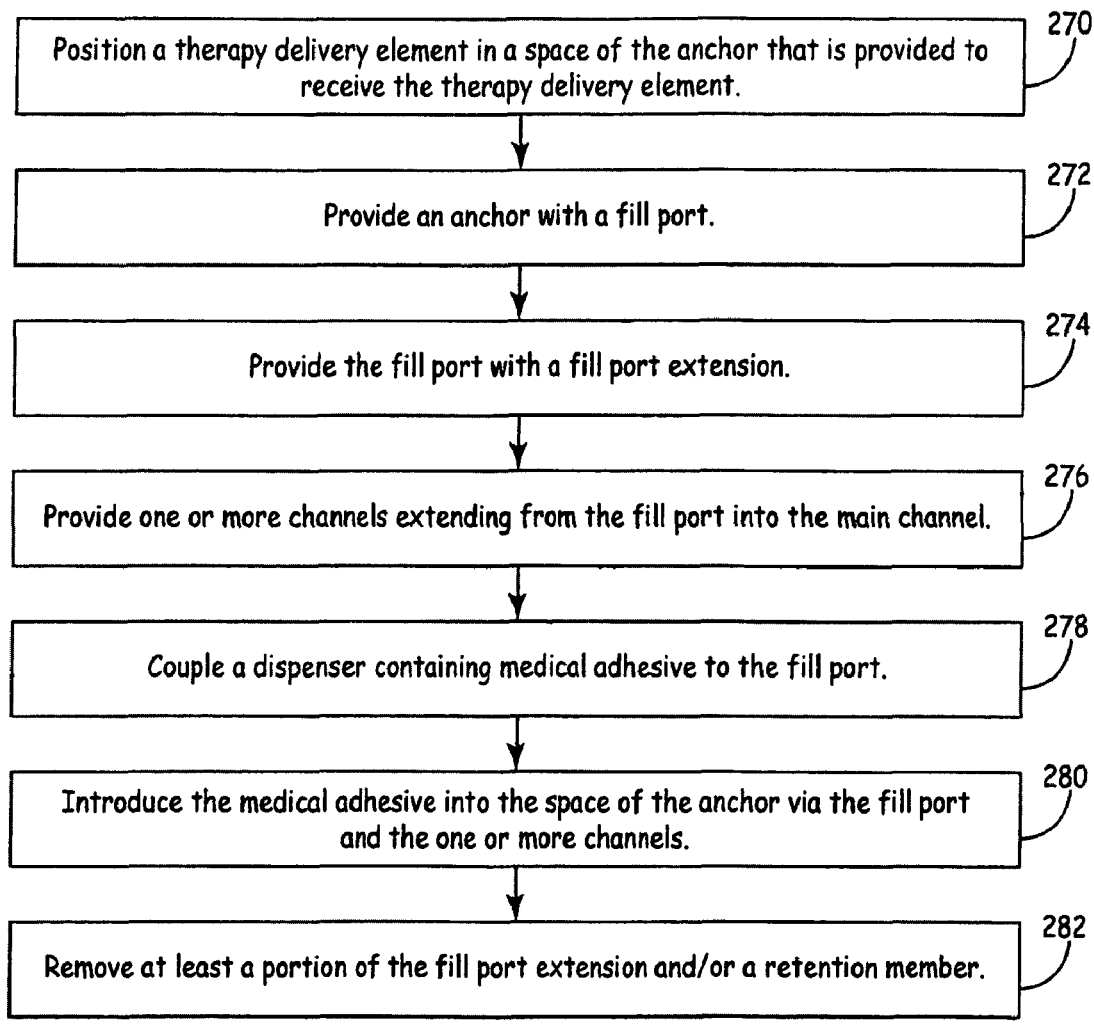
FIG. 19 is a flow diagram of one method according to the current disclosure.

FIG. 19 is a flow diagram of one method according to the current disclosure. A therapy delivery element is positioned in a space of the anchor that is adapted to receive the therapy delivery element (270). In one embodiment, this space is a main channel, but the space may have a shape other than a channel. An anchor is provided with a fill port (272). The fill port may be provided with a fill port extension (274), although in some embodiments, this step may be eliminated. Additionally, one or more side channels may optionally be provided to extend from the fill port into the main channel (276). A dispenser containing medical adhesive may be coupled to the fill port (278), which may be accomplished directly, or in other embodiments indirectly through the use of optional fill port extension. Medical adhesive may then be introduced into the main channel of the anchor via the fill port using one or more additional channels (280).

As discussed above, the step of introducing medical adhesive may be performed during a manufacturing process. In one embodiment, the adhesive is prevented from curing by maintaining the medical adhesive under pressure within fill port extension, one or more port channels, and/or one or more side channels until the time the anchor is deployed. This may involve use of a retention member such as shown and described in reference to FIG. 18.

After the anchor is deployed, and if fill port extensions are provided, at least a portion, or in some cases all, of the fill port extension may then be removed along with any retention member that may have been optionally employed to maintain pre-loaded adhesive within channels of the anchor (282). This may be accomplished, for instance, by cutting the fill port extension from the anchor at the fill port, or at another location along the fill port extension. It will be understood that this method is exemplary only. Many of the steps of this flow diagram may be re-ordered, and many steps may be eliminated entirely.

One skilled in the art will appreciate that the above-described embodiments are exemplary only. For instance, the exemplary figures illustrate a neurostimulator for use with the current system. However, the disclosed anchor may be employed with any type of therapy delivery device, including those for delivering electrical stimulation, a substance to a body, or some other type of treatment. The anchor may include additional features, such as radio-opaque markers to allow the anchor to be visible when x-rays, fluoroscopes, and other similar types of diagnostic tools are utilized. This type of anchor may be used to determine whether the anchor is still in a desired location within the body, for instance.

While the current disclosure describes several exemplary anchor form factors, including anchors that are generally tubular in nature, it will be appreciated that any size, shape, and form factor may be utilized with an anchor as disclosed herein. Moreover, the anchor as described herein is shown to optionally include tabs and/or grooves. However, any other type of fixation mechanism may be provided for use with the disclosed anchor in addition to, or instead of, those shown herein. As another example, any type of connectors may be utilized to couple a dispenser of adhesive to a fill port, to couple an optional fill port extension to a fill port, and/or to couple a dispenser of adhesive to the optional fill port extension. Side channels may, but need not, be provided to uniformly distribute adhesive within a space that is to receive the therapy delivery element. Moreover, if desired, multiple fill ports may be utilized to access different locations of this space that will receive the therapy delivery element to more uniformly distribute the adhesive. Thus, the disclosed system is not to be limited by the foregoing disclosure, which is exemplary, but by the claims that follow.

What is claimed is:

1. An anchor for securing a therapy delivery element in a desired location within a living body, comprising: an anchor body having a space to receive the therapy delivery element; and a fill port provided in the anchor body to introduce an adhesive into the space when the therapy delivery element is positioned within the space; wherein the fill port includes a structure configured to removably couple to a dispenser for dispensing the adhesive, whereby the adhesive affixes the anchor to the therapy delivery element.

2. The anchor of claim 1, further comprising a till port extension having a first end coupled to the fill port, a second end to receive the adhesive, and an intermediate portion to transfer the adhesive to the fill port, whereby the second end may be located a distance from the fill port when the adhesive is dispensed.

3. The anchor of claim 2, wherein the fill port extension includes a connector to receive a dispenser containing the adhesive.

4. The anchor of claim 2, wherein the anchor body includes one or more channels, and wherein the adhesive is pre-loaded into at least one of the fill port extension and the one or more channels.

5. The anchor of claim 1, further comprising multiple channels between the fill port and the space to introduce the adhesive into the space.

6. The anchor of claim 1, wherein the structure comprises threads to engage complementary threads of a dispenser containing the adhesive.

7. The anchor of claim 1, further including multiple fill ports in the anchor body, each to introduce the adhesive into the space.

8. The anchor of claim 7, further including a respective fill port extension coupled to each of the multiple till ports.

9. The anchor of claim 7, wherein the space comprises a main channel that includes first and second ends and wherein a first of the multiple fill ports is located proximate to the first end and a second of the multiple fill ports is located proximate to the second end.

10. The anchor of claim 7, wherein the space comprises a main channel and a first of the multiple fill ports is on one side of the main, channel and a second of the multiple fill ports is on an opposite side of the main channel.

11. The anchor of claim 1, further comprising at least one element to couple the anchor to the living body.

12. The anchor of claim 1, wherein the space includes an enlarged portion to receive the adhesive when the therapy delivery element is located within the space.

13. The anchor of claim 1, wherein the anchor body includes at least one of an RFID tag and a radio-opaque marker.

14. The anchor of claim 1, wherein the structure comprises at least one of a neck extending from a surface of the anchor and one or more threads of a threaded surface.

15. The anchor of claim 1, wherein the structure comprises a fill port extension.

16. The anchor of claim 1, wherein the structure is configured to provide a snap fit with the dispenser.

17. A method for securing a therapy delivery element within a living body, comprising:
positioning an anchor relative to the therapy delivery element;
removably coupling, via a coupling structure of the anchor, a fill port of the anchor to a dispenser of adhesive; and
introducing the adhesive into a space between the anchor and the therapy delivery element via the fill port so that the adhesive affixes the anchor to the therapy delivery element.

18. The method of claim 17, wherein the space comprises a channel, and wherein introducing the adhesive comprises introducing the adhesive along at least a portion of a length of the channel.

19. The method of claim 18, wherein introducing the adhesive comprises introducing the adhesive to multiple points along the channel.

20. The method of claim 17, wherein introducing the adhesive comprises introducing the adhesive into the space via multiple channels extending from the fill port to the space.

21. The method of claim 20, wherein the space comprises a main channel, and wherein introducing the adhesive comprises introducing the adhesive at opposite ends of the main channel via respective ones of the multiple channels.

22. The method of claim 17 wherein introducing the adhesive comprises introducing the adhesive into the space via the fill port extension from a dispenser located at a distance from the fill port.

23. The method of claim 22, wherein introducing the adhesive comprises pre-loading at least one of the anchor and the till port extension with adhesive.

24. The method of claim 17, wherein the anchor is pre-loaded with adhesive that is maintained outside of the space by a retention member and wherein introducing the adhesive comprises removing the retention member after the anchor is in position relative to the therapy delivery element.

25. A system to deliver therapy to a living body, comprising:
a therapy delivery device;
a therapy delivery element extending from the therapy delivery device to deliver therapy to the living body; and
an anchor to receive the therapy delivery element, wherein the anchor comprises a fill port configured to removably couple to a dispenser for dispensing adhesive, whereby the adhesive affixes the anchor to the therapy delivery element.

26. The system of claim 25, wherein the anchor comprises a channel, and wherein the fill port is configured to transfer adhesive along at least a portion of a length of the channel.

27. The system of claim 25, further including a fill port extension providing a conduit to transfer the adhesive to the fill port from a dispenser that is located at a distance from the fill port.

28. The system of claim 27, wherein the fill port extension is removably coupled to the fill port.

29. The system of claim 25, wherein the fill port comprises at least one of a neck extending from a surface of the anchor and one or more threads of a threaded surface.

\* \* \* \* \*

UNITED STATES PATENT AND TRADEMARK OFFICE
CERTIFICATE OF CORRECTION

| | | |
|---|---|---|
| PATENT NO. | : 8,192,406 B2 | Page 1 of 1 |
| APPLICATION NO. | : 12/349065 | |
| DATED | : June 5, 2012 | |
| INVENTOR(S) | : Wells et al. | |

It is certified that error appears in the above-identified patent and that said Letters Patent is hereby corrected as shown below:

Col. 16, Line 33: "comprising a till port" should read --comprising a fill port--

Col. 16, Line 56: "multiple till port" should read --multiple fill ports--

Col. 16, Line 64: "of the main, channel" should read --of the main channel--

Col. 18, Line 7: "and the till port extension" should read --and the fill port extension--

Signed and Sealed this
Twenty-third Day of October, 2012

David J. Kappos
*Director of the United States Patent and Trademark Office*